US010813737B2

(12) United States Patent
Auld et al.

(10) Patent No.: US 10,813,737 B2
(45) Date of Patent: Oct. 27, 2020

(54) MRI COMPATIBLE MAGNETIC SPHINCTER AUGMENTATION DEVICE

(71) Applicants: Torax Medical, Inc., Shoreview, MN (US); Ethicon LLC, Guaynabo, PR (US)

(72) Inventors: Michael D. Auld, Blue Ash, OH (US); Brett E. Swensgard, West Chester, OH (US); Lauren E. Flakne, Cincinnati, OH (US); Kyle P. Taylor, Greenfield, MN (US); Celeste L. Huster, Blaine, MN (US); Jerome K. Grudem, Jr., Rogers, MN (US)

(73) Assignees: Torax Medical, Inc., Shoreview, MN (US); Ethicon LLC, Guaynabo, PR (US)

( * ) Notice: Subject to any disclaimer, the term of this patent is extended or adjusted under 35 U.S.C. 154(b) by 246 days.

(21) Appl. No.: 15/914,407

(22) Filed: Mar. 7, 2018

(65) Prior Publication Data
US 2019/0274803 A1 Sep. 12, 2019

(51) Int. Cl.
*A61F 2/00* (2006.01)
*A61B 17/12* (2006.01)
*A61B 17/00* (2006.01)

(52) U.S. Cl.
CPC ...... *A61F 2/0036* (2013.01); *A61B 17/12009* (2013.01); *A61B 17/12022* (2013.01); *A61B 2017/00827* (2013.01); *A61B 2017/00876* (2013.01); *A61B 2017/12018* (2013.01)

(58) Field of Classification Search
CPC ...... A61F 2/0036; A61F 5/005; A61F 5/0069; A61B 17/12009; A61B 17/12013; A61B 2017/00827; A61B 2017/12018

USPC ........................................................ 600/9–15
See application file for complete search history.

(56) References Cited

U.S. PATENT DOCUMENTS

| 6,543,456 | B1 | 4/2003 | Freeman |
| 7,175,589 | B2 | 2/2007 | Deem et al. |
| 7,445,010 | B2 | 11/2008 | Kugler et al. |
| 7,695,427 | B2 | 4/2010 | Kugler et al. |
| 8,070,670 | B2 | 12/2011 | Deem et al. |
| 8,603,023 | B2 | 12/2013 | Albrecht et al. |
| 8,617,049 | B2 | 12/2013 | Dlugos, Jr. et al. |
| 8,636,751 | B2 | 1/2014 | Albrecht et al. |
| 8,734,475 | B2 | 5/2014 | Ekvall et al. |
| 8,870,742 | B2 | 10/2014 | Dlugos, Jr. et al. |
| 8,876,761 | B2 | 11/2014 | Albrecht et al. |

(Continued)

OTHER PUBLICATIONS

U.S. Appl. No. 15/664,665, entitled "Method for Assisting a Sphincter," filed Jul. 31, 2017.

*Primary Examiner* — Samuel G Gilbert
(74) *Attorney, Agent, or Firm* — Frost Brown Todd LLC

(57) ABSTRACT

An apparatus includes a plurality of beads and a plurality of links joining the beads together. Each bead includes a housing, a passageway extending through the housing, and at least one annular magnet. The passageway defines an axis. The at least one annular magnet is coaxially positioned about the passageway. The housing defines a gap adjacent to the at least one annular magnet. The gap is sized and configured to allow at least one annular magnet to rotate relative to the housing about a rotation axis. The rotation axis is offset from the axis of the passageway. Portions of the links are slidably disposed in corresponding passageways of the beads.

20 Claims, 9 Drawing Sheets

(56) References Cited

U.S. PATENT DOCUMENTS

2005/0283235 A1* 12/2005 Kugler ............. A61B 17/12009
623/14.13
2011/0098731 A1  4/2011 Whitbrook et al.
2011/0270019 A1* 11/2011 Deuel ................... A61F 5/0056
600/37

* cited by examiner

MRI COMPATIBLE MAGNETIC SPHINCTER AUGMENTATION DEVICE

FIELD OF THE INVENTION

The invention pertains to a sphincter augmentation device. More specifically, the invention pertains to a sphincter augmentation device that may compatible with a magnetic resonance imaging ("MRI") machine.

BACKGROUND

In some instances, it may be desirable to place a medical implant within or surrounding a biological lumen/passageway in order to improve or assist the function of, or otherwise affect, the biological lumen/passageway. Examples of such biological lumens/passageways include, but are not limited to, the esophagus, a fallopian tube, a urethra, or a blood vessel. Some biological passages normally function by expanding and contracting actively or passively to regulate the flow of solids, liquids, gasses, or a combination thereof. The ability of a biological passage to expand and contract may be compromised by defects or disease. One merely illustrative example of a condition associated with decreased functionality of a body passage is Gastro Esophageal Reflux Disease ("GERD"), which effects the esophagus.

A normal, healthy, esophagus is a muscular tube that carries food from the mouth, through the chest cavity and into the upper part of the stomach. A small-valved opening in the esophagus, called the lower esophageal sphincter ("LES"), regulates the passage of food from the esophagus into the stomach, as well as the passage of acidic fluids and food from the stomach toward the esophagus. The LES may also regulate stomach intra-gastric pressures. A healthy LES may contain pressure of gasses within the stomach at around 10 mm Hg greater than normal intragastrical pressure, thereby impeding acidic gases/fluids from refluxing from the stomach back into the esophagus. When functioning properly, a pressure difference greater than 10 mm Hg may regulate when the LES opens to allow gasses to be vented from the stomach toward the esophagus.

If the LES relaxes, atrophies, or degrades for any reason, the LES may cease functioning properly. Therefore, the LES may fail to sufficiently contain pressure of gasses within the stomach such that acidic contents of the stomach may travel back into the esophagus, resulting in reflux symptoms. Two primary components that control the LES are the intrinsic smooth muscle of the distal esophagus wall and the skeletal muscle of the crural diaphragm or esophageal hiatus. A causation of esophageal reflux, which may be associated with GERD, is relaxation of one or both of the smooth muscle of the distal esophagus wall or the hiatal diaphragm sphincter mechanisms. Chronic or excessive acid reflux exposure may cause esophageal damage. Conventionally, treatment for GERD may involve either open or endoscopic surgical procedures. Some procedures may include a fundoplication that mobilizes of the stomach relative to the lower esophagus, or suturing a pleat of tissue between the LES and the stomach to make the lower esophagus tighter.

Examples of devices and methods that have been developed to treat anatomical lumens by providing sphincter augmentation are described in U.S. Pat. No. 7,175,589, entitled "Methods and Devices for Luminal and Sphincter Augmentation," issued Feb. 13, 2007, the disclosure of which is incorporated by reference herein; U.S. Pat. No. 7,695,427, entitled "Methods and Apparatus for Treating Body Tissue Sphincters and the Like," issued Apr. 13, 2010, the disclosure of which is incorporated by reference herein; U.S. Pat. No. 8,070,670, entitled "Methods and Devices for Luminal and Sphincter Augmentation," issued Dec. 6, 2011, the disclosure of which is incorporated by reference herein; and U.S. Pat. No. 8,734,475, entitled "Medical Implant with Floating Magnets," issued May 27, 2014, the disclosure of which is incorporated by reference herein.

While various kinds and types of instruments have been made and used to treat or otherwise engage anatomical lumens, it is believed that no one prior to the inventors has made or used an invention as described herein.

SUMMARY OF THE INVENTION

An apparatus includes a plurality of beads and a plurality of links joining the beads together. Each bead includes a housing, a passageway extending through the housing, and at least one annular magnet. The passageway defines an axis. The at least one annular magnet is coaxially positioned about the passageway. The housing defines a gap adjacent to the at least one annular magnet. The gap is sized and configured to allow at least one annular magnet to rotate relative to the housing about a rotation axis. The rotation axis is offset from the axis of the passageway. Portions of the links are slidably disposed in corresponding passageways of the beads.

An apparatus includes a plurality of beads and a plurality of links. Each bead includes a housing defining an axis and a magnet receiving space and at least one annular magnet. The at least one annular magnet is coaxially positioned about the axis and in the magnet receiving space. The magnet receiving space is sized to provide a gap adjacent to the at least one annular magnet. The gap is sized and configured to allow at least one annular magnet to rotate relative to the housing about a rotation axis. The rotation axis is offset from the axis of the housing. The links join the beads together.

An apparatus includes a plurality of beads and a plurality of links. Each bead comprises a housing defining a longitudinal axis and at least one annular magnet. The at least one annular magnet is coaxially positioned in the housing about the longitudinal axis. The links join the beads together. The apparatus further includes a means for permitting the at least one annular magnet to rotate relative to the housing about a rotation axis. The rotation axis is offset from the longitudinal axis of the housing.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

Figure 1:
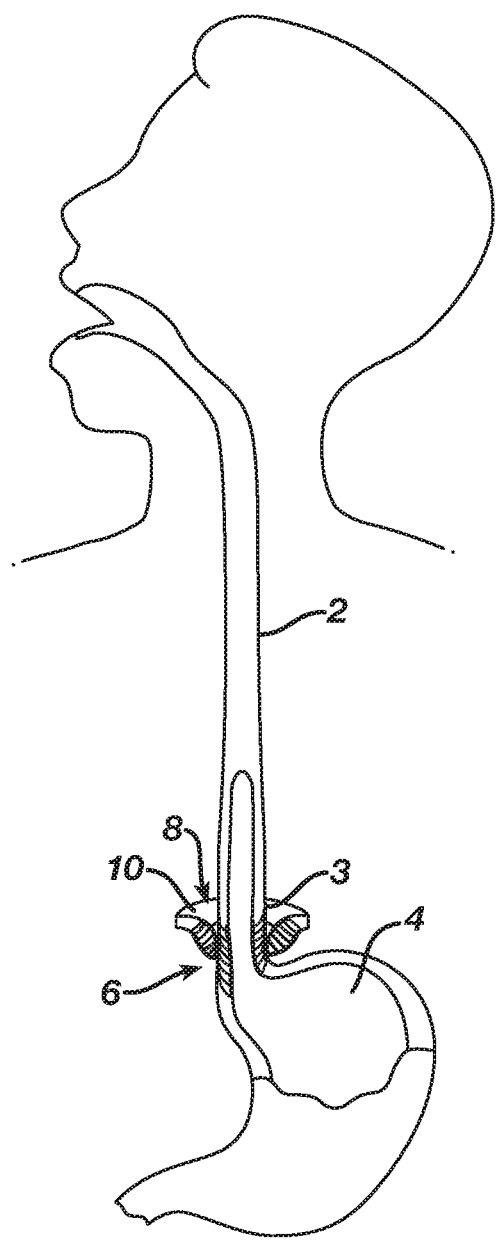
FIG. 1 depicts a cross-sectional side view, taken along a coronal plane of the body, of a biological passage.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

I. Overview of Exemplary Sphincter Augmentation Device

Figure 2:
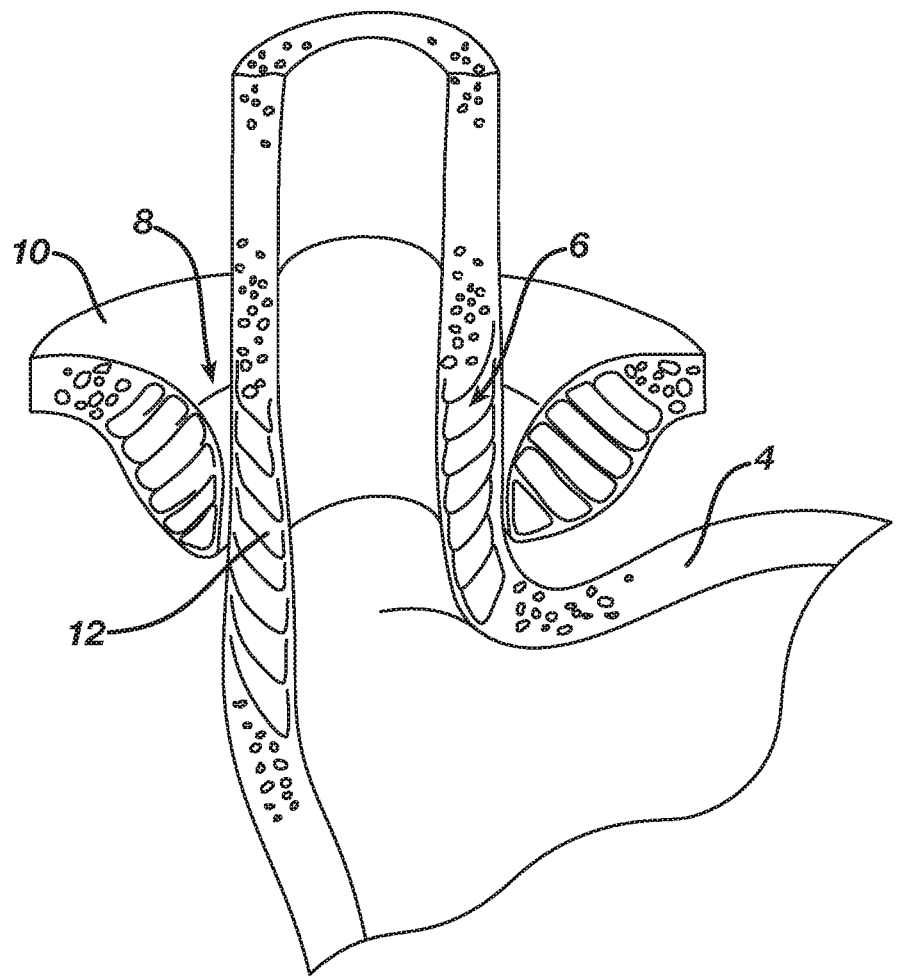
FIG. 2 depicts a cross-sectional isometric view, taken along a coronal plane of the body, of a human esophagogastric junction.
Figure 3:
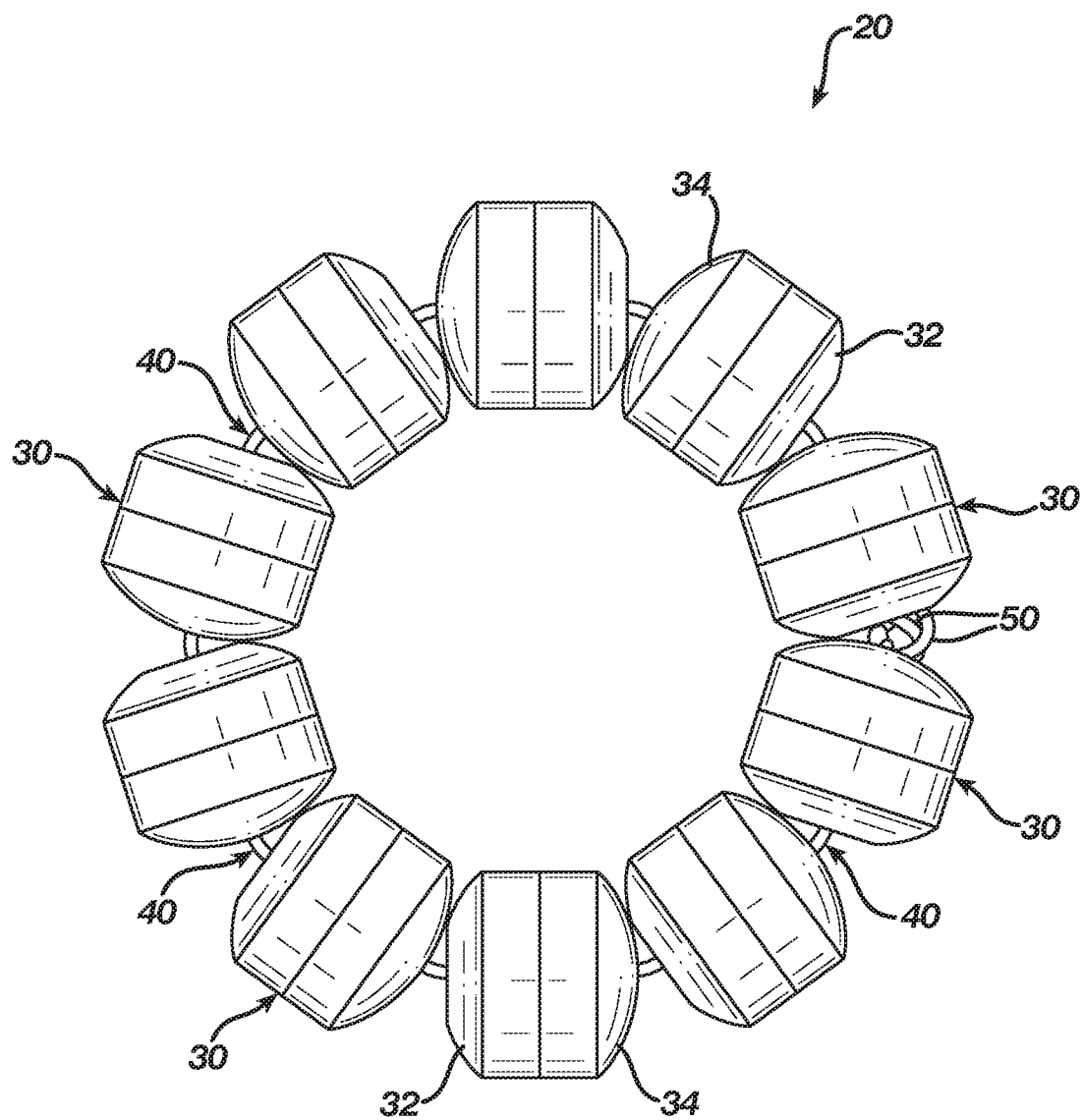
FIG. 3 depicts a top plan view of an exemplary sphincter augmentation device.

FIGS. 1-2 show selected portions of human anatomy, which includes an esophagus (2) extending from the mouth, through a hiatus (8) defined by a diaphragm (10), and into a stomach (4). Esophagus (2) also includes a distal esophagus (3) and an LES (6). LES (6) is located along distal esophagus (3) adjacent to the junction of esophagus (2) and stomach (4). The portion of LES (6) extending through hiatus (8) is supported by diaphragm (10). When functioning properly, LES (6) is configured to transition between an occluded state and an opened state (as shown in FIG. 2). As best seen in FIG. 2, LES (6) includes a plurality of sling fibers (12). Sling fibers (12) are smooth muscle tissue that may help regulate LES (6) transition between the occluded state and the open state. Hiatus (8) of diaphragm (10) may also help LES (6) transition between the occluded state and the open state.

A healthy LES (6) transitions between the occluded state and the opened state to act as a valve. In other words, a healthy LES (6) may transition from the occluded state to the opened state to allow solids, liquids, and/or gasses to selectively travel between esophagus (2) and stomach (4). For example, a healthy LES (6) may transition from the occluded state to the opened state to permit a bolus of food to travel from esophagus (2) into stomach (4) during peristalsis; or to vent intra-gastric pressure from stomach (4) toward esophagus (2). Additionally, in the occluded state, a healthy LES (6) may prevent digesting food and acidic fluid from exiting stomach (4) back into esophagus (2).

If LES (6) ceases functioning properly by prematurely relaxing, and thereby improperly transitioning esophagus (2) from the occluded state to the opened state, undesirable consequences may occur. Examples of such undesirable consequences may include acidic reflux from stomach (4) into esophagus (2), esophageal damage, inflamed or ulcerated mucosa, hiatal hernias, other GERD symptoms, or other undesirable consequences as will be apparent to one having ordinary skill in the art in view of the teachings herein. Therefore, if an individual has an LES (6) that prematurely relaxes, causing improper transitions from the occluded state to the opened state, it may be desirable to insert an implant around a malfunctioning LES (6) such that the implant and/or LES (6) may properly transition between the occluded state and the opened state.

Figure 4:
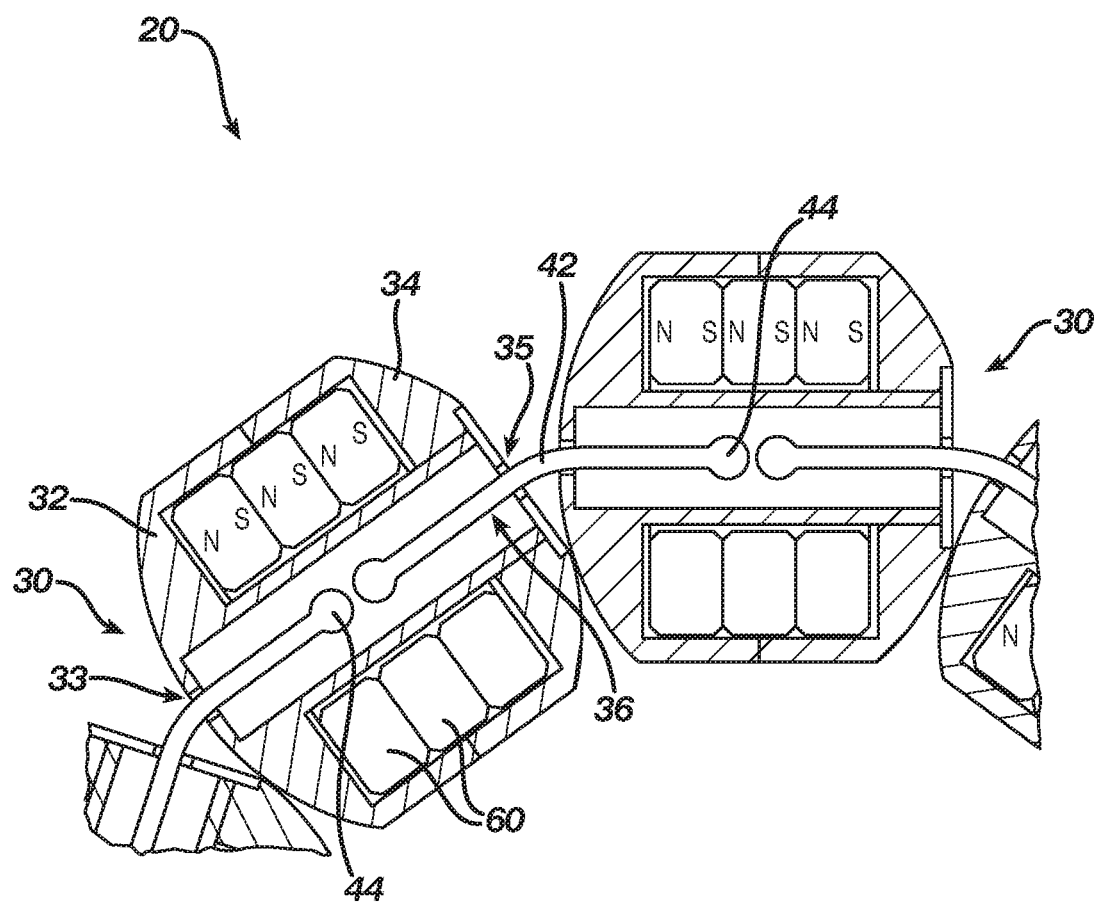
FIG. 4 depicts a partial, cross-sectional view of a portion of the sphincter augmentation device of FIG. 3.

FIGS. 3-5B show an exemplary sphincter augmentation device (20) that may be used as an implant around a malfunctioning LES (6) to assist the LES (6) in transitioning between the occluded state and the opened state. Device (20) of this example comprises a plurality of beads (30) that are joined together by a plurality of links (40). Each bead (30) comprises a pair of housings (32, 34) that are securely fastened to each other. By way of example only, housings (32, 34) may be formed of a non-ferrous material (e.g., titanium, plastic, etc.). Each bead (30) further comprises a plurality of annular or toroidal rare-earth permanent magnets (60) that are stacked next to each other within housings (32, 34). In the present example, magnets (60) are completely sealed within beads (30). As best seen in FIG. 4, each bead (30) also defines a chamber (36) that is configured to receive a portion of a respective pair of links (40). Housing (32) defines an opening (32) at one end of chamber (36); while housing (34) defines an opening (35) at the other end of chamber (36).

Each link (40) of the present example comprises a wire (42) that is pre-bent to form an obtuse angle. The free end of each wire (42) terminates in a ball tip (44). Beads (30) are joined together by links (40) such that a first end portion of a link (40) is in one bead (30), a second end portion of the same link (40) is in another bead (30), and an intermediate portion of the same link (40) is positioned between those two beads (30). Chambers (36) of beads (30) are configured to freely receive ball tips (44) and adjacent regions of wires (42); while openings (33, 35) are configured to prevent ball tips (44) from exiting chambers (36). Openings (33, 35) are nevertheless sized to allow wire (42) to slide through openings (33, 35). Thus, links (40) and beads (30) are configured to allow beads (30) to slide along lengths (40) through a restricted range of motion.

Figure 5A:
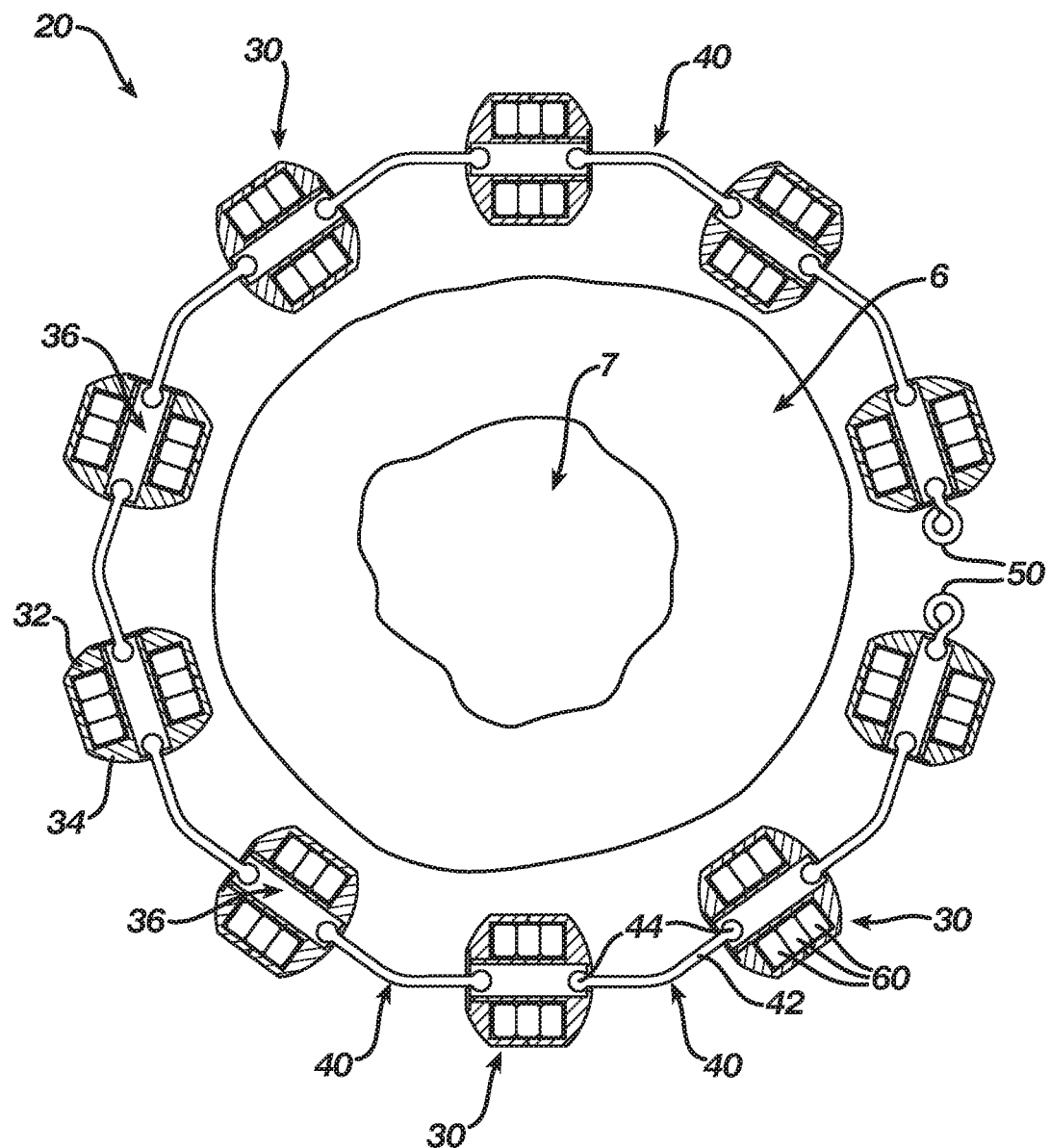
FIG. 5A depicts a top, cross-sectional view of the sphincter augmentation device of FIG. 3 positioned about an LES, with the sphincter augmentation device in an open and expanded configuration.
Figure 5B:
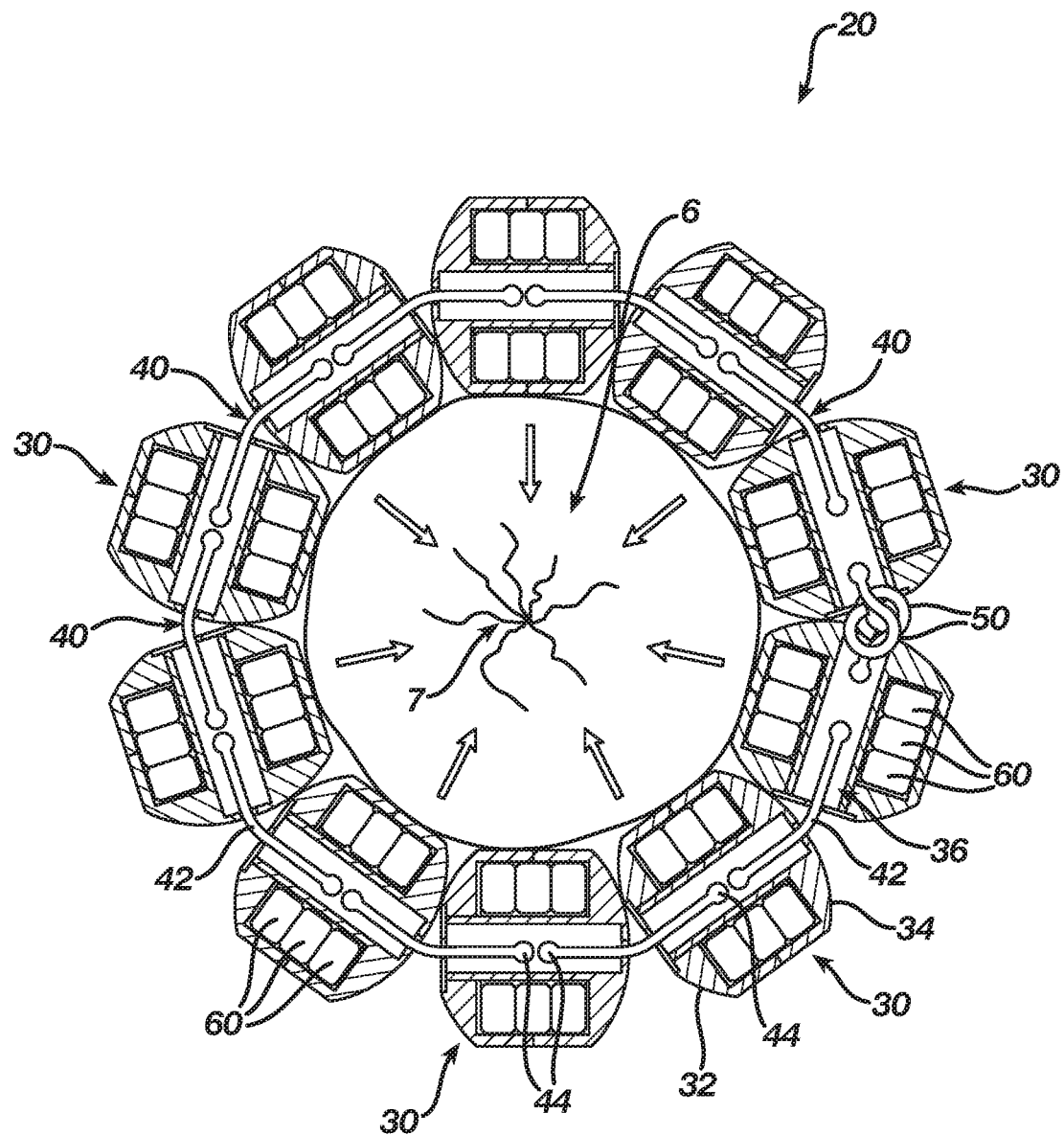
FIG. 5B depicts a top, cross-sectional view of the sphincter augmentation device of FIG. 3 positioned about the LES of FIG. 5A, with the sphincter augmentation device in a closed and contracted configuration.

As best seen in FIGS. 5A-5B, two beads (30) have opposing fastener features (50) that allow the ends of device (20) to be coupled together to form a loop. In the present example, fastener features (50) comprise eyelets. In some other versions, fastener features (50) comprise complementary clasp features. As another merely illustrative example, fastener features (50) may be configured and operable in accordance with one or more of the teachings of U.S. patent application Ser. No. 15/664,665, entitled "Method for Assisting a Sphincter," filed Jul. 31, 2017, issued as U.S. Pat. No. 10,405,865 on Sep. 10, 2019, the disclosure of which is incorporated by reference herein. Other suitable ways in which the ends of device (20) may be coupled together to form a loop will be apparent to those of ordinary skill in the art in view of the teachings herein. Those of ordinary skill in the art will also recognize that it may be desirable to provide fastener features (50) that can be decoupled if it becomes necessary or otherwise warranted to remove device (20) from the patient.

FIG. 5A shows device (20) in an open, expanded state, with device (20) being positioned about LES (6). At this stage, the opening (7) defined by LES (6) is in a persistently open state (e.g., allowing the patient to undesirably experience GERD and/or other undesirable conditions), warranting the securement of device (20) about the LES (6). FIG. 5B shows device (20) secured about the LES (6), with device (20) in a closed, contracted state. Device (20) is secured closed via fastener features (50). Magnets (60) are oriented within beads (30) such that each bead (30) will be magnetically attracted to the adjacent bead (30) in device (20). In other words, beads (30) are magnetically attracted to each other to magnetically bias device (20) toward the contracted configuration shown in FIG. 5B.

With device (20) secured around the LES (6) and in the contracted configuration, device (20) deforms the LES (6) radially inwardly to substantially close the opening defined by the LES (6). In doing so, device (20) prevents the patient from experiencing GERD and/or other undesirable conditions that may be associated with a persistently open opening (7) at the LES (6). While magnets (60) have a tesla value that is high enough to substantially maintain opening (7) in a closed state to the point of preventing GERD and/or other undesirable conditions that may be associated with a persistently open opening (7), the tesla value of magnets (60) is low enough to allow LES (6) to expand radially outwardly to accommodate passage of a bolus of food, etc. through the opening (7) of LES (6). To accommodate such expansion, beads (30) may simply slide along links (40) to enlarge the effective diameter of device (20) as the bolus passes. After the bolus passes, the magnetic bias of magnets (60) will return device (20) to the contracted state shown in FIG. 5B. Device (20) thus ultimately prevents GERD and/or other undesirable conditions that may be associated with a persistently open opening (7); while still permitting the normal passage of food, etc. from the esophagus (2) to the stomach (4).

In addition to the foregoing, device (20) may be constructed and operable in accordance with at least some of the teachings of U.S. Pat. No. 7,695,427, the disclosure of which is incorporated by reference herein; and/or U.S. patent application Ser. No. 15/664,665, entitled "Method for Assisting a Sphincter," filed Jul. 31, 2017, issued as U.S. Pat. No. 10,405,865 on Sep. 10, 2019, the disclosure of which is incorporated by reference herein.

Figure 6A:
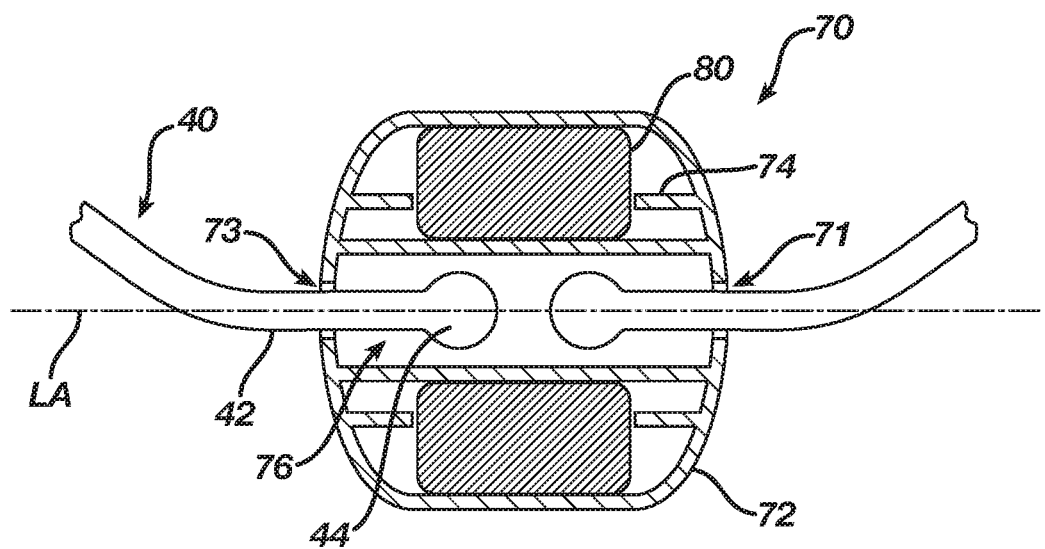
FIG. 6A depicts a top, cross-sectional view of a bead assembly and portions of links of another exemplary sphincter augmentation device.
Figure 6B:
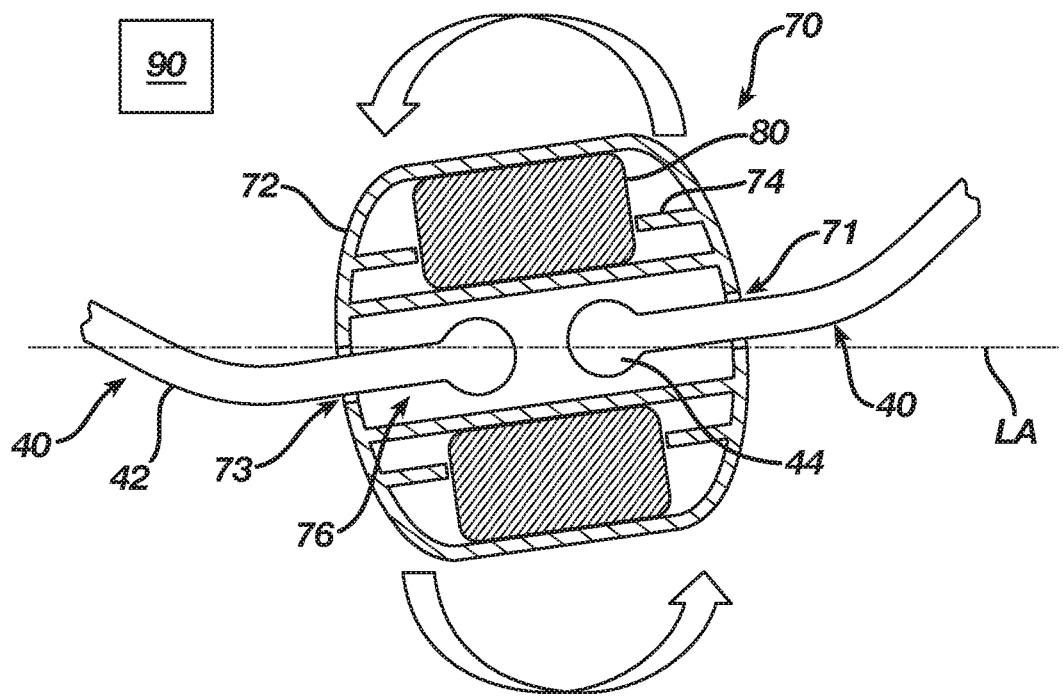
FIG. 6B depicts a top, cross-sectional view of the bead assembly and links of FIG. 6A in the presence of an activated MRI machine.

II. Exemplary Use of Sphincter Augmentation Device in Magnetic Field Generated by MRI Machine FIGS. 6A-6B show a merely illustrative variation of bead (30). In particular, FIGS. 6A-6B show an exemplary bead (70) that includes a housing (72) defining a chamber (76) that terminates in a pair of opposing openings (71, 73). An annular rare-earth permanent magnet (80) is contained within housing (72). Ball ends (44) of two links (40) are slidably disposed in chamber (76), with openings (71, 73) being sized to prevent ball ends (44) from exiting chamber (76) while permitting wires (42) of links (40) to slide through openings (71, 73). Bead (70) is thus substantially identical to bead (30). Those of ordinary skill in the art will therefore understand that a sphincter augmentation device may be formed using beads (70), and that such a sphincter augmentation device may be operable just like device (20), with beads (70) being substituted for beads (30).

Housing (72) includes internal boss structures (74) that maintain constant contact with magnet (80). Due to the presence of boss structures (74), magnet (80) is incapable of moving within housing (72). Incidentally, as shown in FIG. 4, housings (32, 34) are also configured to maintain constant contact with magnets (60), such that magnets (60) are incapable of moving within housings (32, 34). This immobility of magnets (60, 80) within housings (32, 34, 72) may create undesirable conditions if beads (20, 30) ever encounter a substantially powerful magnetic field, such as the magnetic field generated by an MRI machine. Such exposure may occur when a patient in whom a device (20) is installed gets scanned by an MRI machine.

FIG. 6B depicts an example of a result that might occur when bead (70) is exposed to a substantially powerful magnetic field generated by an MRI machine (90). For instance, "substantially powerful" in this context may include a magnetic field of at least 0.7 Tesla, or more particularly at least 1.5 Tesla, or even more particularly at least 3 Tesla. Due to the difference between the orientation of the magnetic field of the MRI machine (90) and the orientation of the magnetic field of magnet (80), the magnetic field generated by an MRI machine (90) causes magnet (80) to rotate about an axis that is perpendicular to the longitudinal axis (LA) passing through the central opening defined by magnet (80) (i.e., the same longitudinal axis (LA) passing through the center of passageway (76)). In particular, when magnets (80) are positioned within the substantial magnetic field of an MRI machine (90), any magnets (80) that are in that substantial magnetic field may be suddenly biased to align with the magnetic field of the MRI machine (90). While magnets (80) that are already aligned with the magnetic field of the MRI machine (90) may remain stationary, the other magnets (80) may be magnetically urged to rotate about respective axes to achieve alignment with the magnetic field of the MRI machine (90). In some scenarios, approximately half of the magnets (80) in a sphincter augmentation device may be already aligned with the magnetic field of the MRI machine (90), while the rest of the magnets (80) in the same sphincter augmentation device may be magnetically urged to rotate to achieve alignment with the magnetic field of the MRI machine (90).

With magnet (80) being snugly fit within housing (72) due to the presence and configuration of boss structures (74), the above-described rotation of magnet (80) is directly communicated to housing (72), such that housing also rotates about the same axis. Those of ordinary skill in the art will recognize that similar rotation or twisting may occur with at least some other beads (70) that bead (70) is joined with via links (40). Those of ordinary skill in the art will also recognize that similar rotation or twisting may occur among beads (30) of device (20) when device (20) is exposed to a substantially powerful magnetic field generated by an MRI machine (90).

Figure 7A:
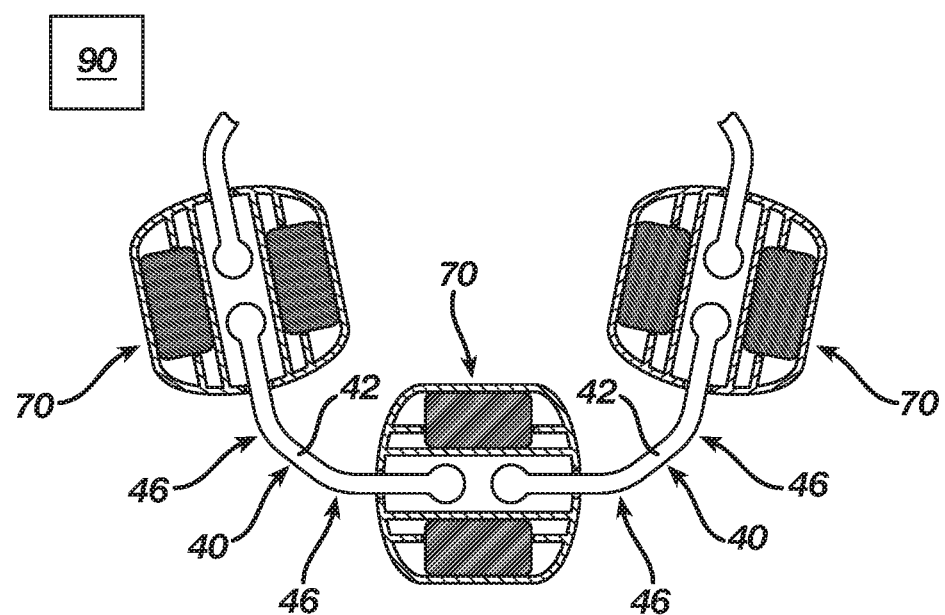
FIG. 7A depicts a top, cross-sectional view of several bead assemblies and links of the sphincter augmentation device of FIG. 6A in the presence of a magnetic field of an MRI machine.
Figure 7B:
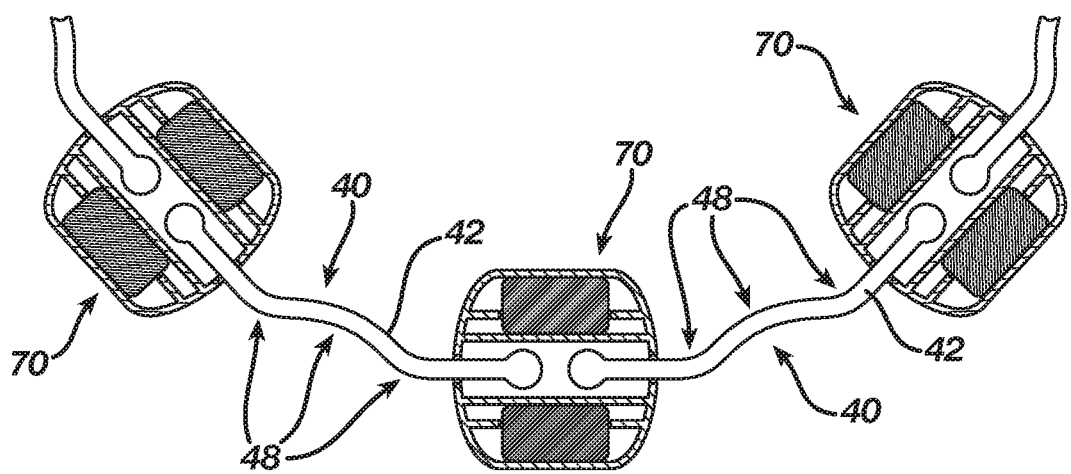
FIG. 7B depicts a top, cross-sectional view of the bead assemblies and links of FIG. 7A after removal from the presence of the magnetic field of the MRI machine.

FIGS. 7A-7B show a potential result that may occur when a plurality of joined beads (70) are subject to rotation or twisting due to a powerful magnetic field generated by an MRI machine (90). While FIGS. 7A-7B show beads (70) in the absence of a LES (6), the LES (6) is omitted from FIGS. 7A-7B for the sake of clarity. The phenomena depicted in FIGS. 7A-7B may still occur when a plurality of beads (70) are secured about an LES (6) in a closed-loop configuration. FIG. 7A shows beads (70) and links (40) during activation of MRI machine (90), such that beads (70) and links (40) are exposed to a substantial magnetic field. As noted above, the magnetic field causes magnets (80) to rotate about respective perpendicular axes, which in turn causes beads (70) to rotate about respective perpendicular axes. In this example, the axes of rotation are substantially parallel with each other. Moreover, if beads (70) were shown in a full set of beads (70) encircling an LES (6), the axes of rotation would be substantially parallel with the central longitudinal axis of the esophagus (2). Alternatively, the axes of rotation may be oblique relative to the central longitudinal axis of the esophagus (2). In either case, the axes of rotation are oriented such that the loop formed by beads (70) deforms.

As shown in FIG. 7A, the deformation of the loop formed by beads (70) as a result of the magnetic field from MRI machine (90) causes the formation of several bends (46) in each link (40). In some instances, bends (46) provide plastic deformation of links (40). FIG. 7B shows beads (70) and links (40) after beads (70) and links (40) have been removed from the magnetic field of MRI machine (90) (e.g. after MRI machine (90) is deactivated). As shown, links (40) now include several kinks (48) after encountering the deformation caused by the rotation of beads (70) and corresponding bending (46) of wires (42) due to the magnetic field of MRI machine (90).

With links (40) including kinks (48) as shown in FIG. 7B, a sphincter augmentation device formed by beads (70) and deformed links (40) may no longer serve its purpose appropriately. For instance, kinks (48) may prevent links (40) from sufficiently sliding through openings (71, 73). If links (40) cannot sufficiently slide through openings (71, 73), beads (70) may be unable to come into close enough proximity to each other to form a substantially closed configuration like the configuration shown in FIG. 5B. If beads (70) are unable to come into close enough proximity to each other to form a substantially closed configuration like the configuration shown in FIG. 5B, opening (7) of the LES (6) may not reach a sufficiently closed state, such that the patient may continue to experience GERD and/or other undesirable conditions associated with a persistently open opening (7) of the LES (6). In some other circumstances, kinks (48) may deform the entire loop formed by beads (70) and links (40) to the point where the loop does not sufficiently expand when a bolus of food, etc., reaches the opening (7) of the LES (6). This may result in dysphagia and/or other results associated with an opening (7) of the LES (6) that is either persistently closed or does not otherwise open enough to a desirable degree.

In addition to potentially causing kinks (48), exposing beads (30, 70) to a substantial magnetic field from an MRI machine (90) may also cause at least some degree of demagnetization of magnets (60, 80) (e.g., when the magnetic field of the MRI machine (90) exceeds the intrinsic coercivity property (HCi) of magnet (60, 80)). As noted above, magnets (60, 80) may be magnetically biased to align with the substantial magnetic field from an MRI machine (90), such that any misaligned magnets (60, 80) may rotate. The containment of magnets (60, 80) in housing (32, 34, 72), and the coupling of beads (30, 70) with links (40) may prevent magnets (60, 80) from achieving full alignment with the substantial magnetic field from an MRI machine (90), even when a plurality of bends (46) are formed in wires (42). When magnets (60, 80) are unable to achieve full alignment with the substantial magnetic field from the MRI machine (90), the substantial magnetic field of the MRI machine (90) may cause at least some degree of demagnetization of magnets (60, 80). When one or more magnets (60, 80) of a sphincter augmentation device are at least partially demagnetized, the affected beads (30, 70) might not be able to come into close enough proximity to each other to form a substantially closed configuration like the configuration shown in FIG. 5B, such that opening (7) of the LES (6) may not reach a sufficiently closed state, and such that the patient may continue to experience GERD and/or other undesirable conditions associated with a persistently open opening (7) of the LES (6).

In view of the foregoing, it may be desirable to provide a variation of beads (30, 70) and/or links (40) that prevents (or at least reduces the likelihood of) the formation of kinks (48) and/or the demagnetization of magnets (60, 80). Such a variation of sphincter augmentation device (20) may provide a sphincter augmentation device that is more compatible with an MRI machine (90), enabling patients who are fitted with the sphincter augmentation device to be scanned in an MRI machine without adversely affecting the performance of the sphincter augmentation device. One merely illustrative variation of sphincter augmentation device (20) may include the use of nitinol or some other superelastic material to form links (40). In some such variations, a sphincter augmentation device (20) incorporating links (40) formed of nitinol may still deform in a manner similar to that shown in FIG. 7A when the sphincter augmentation device is exposed to the substantial magnetic field of MRI machine (90). However, the superelasticity of the nitinol may provide greater tolerance to the deformation at bends (46). Thus, when the variation of sphincter augmentation device (20) is removed from the magnetic field of MRI machine (90), nitinol links (40) may lack kinks (48) of FIG. 7B; and may instead return to a normal configuration with a single bend, like the configuration shown in FIGS. 4-5B.

Figure 8A:
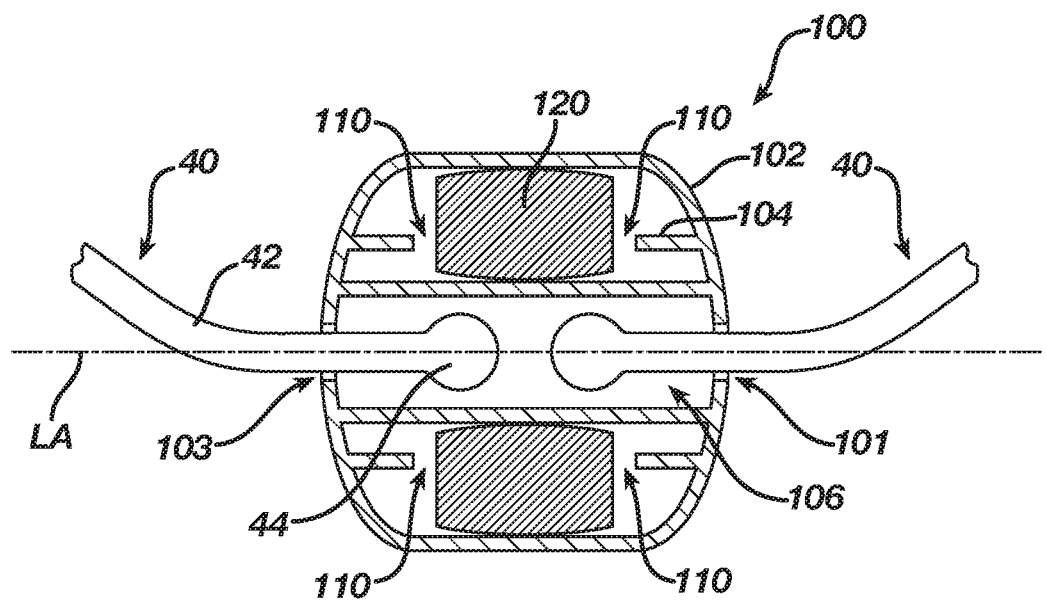
FIG. 8A depicts a top, cross-sectional view of a bead assembly and portions of links of yet another exemplary sphincter augmentation device.
Figure 8B:
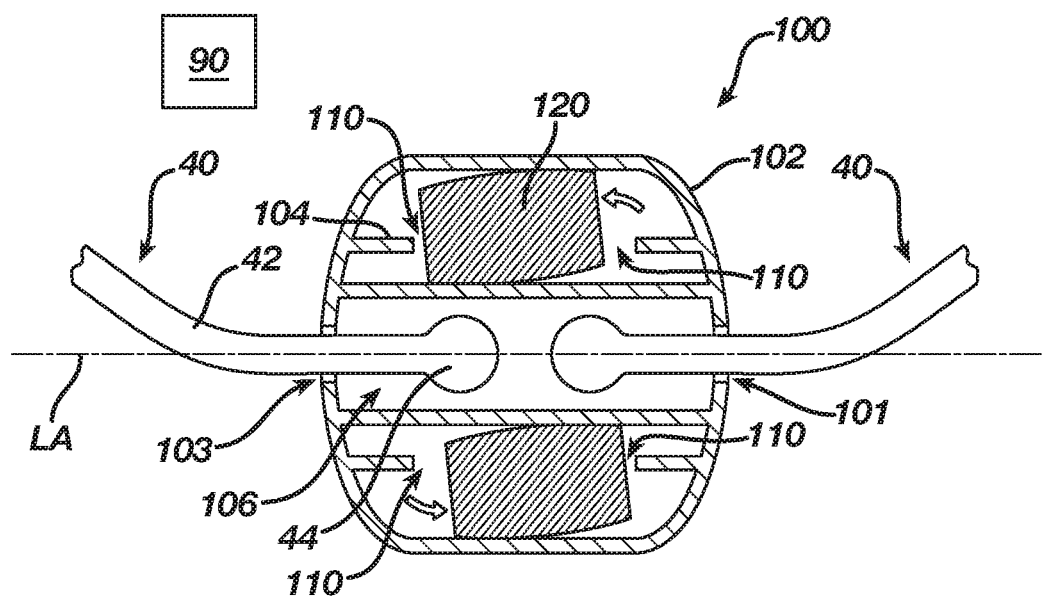
FIG. 8B depicts a top, cross-sectional view of the bead assembly and links of FIG. 8A in the presence of the magnetic field of an MRI machine.

As another merely illustrative example, housings (32, 34, 72) may be modified to accommodate movement of magnets (60, 80) with respect to housings (32, 34, 72). FIGS. 8A-8B show an example of such a variation. In particular, FIGS. 8A-8B show a bead (100), which serves as a variation of beads (30, 70). Bead (100) of this example includes a housing (102) defining a chamber (106) that terminates in a pair of opposing openings (101, 103). An annular rare-earth permanent magnet (120) is contained within housing (102). Ball ends (44) of two links (40) are slidably disposed in chamber (106), with openings (101, 103) being sized to prevent ball ends (44) from exiting chamber (106) while permitting wires (42) of links (40) to slide through openings (101, 103). Bead (100) is thus similar to beads (30, 70). Those of ordinary skill in the art will therefore understand that a sphincter augmentation device may be formed using beads (100), and that such a sphincter augmentation device may be operable just like device (20), with beads (100) being substituted for beads (30).

Like housing (72), housing (102) of the present example includes internal boss structures (104). However, unlike internal boss structures (74) of bead (72), internal boss structures (104) of housing (102) define gaps (110) adjacent to magnet (120), such that internal boss structures (104) do not maintain constant contact with magnet (120). Gaps (110) are sized and configured to allow magnet (120) to rotate within housing (102) about an axis that is perpendicular to longitudinal axis (LA). Thus, when a variation of sphincter augmentation device (20) incorporating beads (100) is subject to a substantial magnetic field generated by an MRI machine (90), gaps (110) provide freedom for magnets (120) to rotate within housing (102), as shown in FIG. 8B.

In the present example, the amount of rotation permitted by gaps (110) is somewhat slight. However, the amount of rotation permitted by gaps (110) is sufficient to prevent or reduce rotation of housing (102) when beads (100) are subject to a substantial magnetic field generated by an MRI machine (90). When rotation of housing (102) is prevented or reduced, the deformation of links (40) is prevented or reduced when beads (100) are subject to a substantial magnetic field generated by an MRI machine (90). Thus, by accommodating at least some rotation of magnet (120) relative to housing (102), bead (100) is configured to prevent or reduce deformation of links (40). By preventing or reducing deformation of links (40) in a magnetic field generated by an MRI machine (90), the formation of kinks (48) in links (40) is prevented (or the likelihood of kinks (48) forming in links (40) is at least reduced). This avoidance of kink (48) formation may be further enhanced by combining the use of nitinol to form links (40) with the incorporation of gaps (110) within housing (102).

In addition to preventing or reducing the likelihood of kink (48) formation, the added rotatability of magnets (120) in housings (102) may prevent or reduce the effect of demagnetization. In other words, by providing magnets (120) with greater freedom to align with the magnetic field of MRI machine (90), the magnetic strain imposed on magnets (120) by the magnetic field of MRI machine (90) is reduced or eliminated, thereby reducing or eliminating the demagnetization effect that might otherwise be encountered in magnets that are unable (or otherwise less able) to align with the magnetic field of MRI machine (90).

As yet another potential result from gaps (110) allowing magnets (120) to rotate in housings (102), a sphincter augmentation device that incorporates beads (100) may be less likely than sphincter augmentation device (20) to substantially deform the patient's LES (6) when the patient is placed in the magnetic field of the MRI machine (90). When a patient with sphincter augmentation device (20) is placed in the magnetic field of the MRI machine (90), at least some of the beads (30) may rotate as described above, as magnets (60) attempt to align with the magnetic field of the MRI machine (90). As these beads (30) rotate, the rotation of beads (30) may reduce the effective diameter of device (20), thereby causing radially inward compression of the LES (6), which may cause patient discomfort. If magnets (120) are permitted to rotate within housings (102) as in beads (100), this relative rotation may prevent or at least reduce rotation of beads (100), which may in turn prevent or at least reduce the additional radial inward compression of the LES (6) when the patient is placed in the magnetic field of the MRI machine (90) with a sphincter augmentation device incorporating beads (100).

The foregoing variations of using a superelastic material (e.g., nitinol, etc.) to form links (40) and/or to provide gaps (110) that accommodate some degree of rotation of magnets (120) within housings may thus provide at least three different aspects of MRI compatibility by allowing magnets (120) to at least partially align with the magnetic field of an MRI machine (90). First, these variations may prevent kinks (48) from forming in links (40) or at least reduce the likelihood of kinks (48) forming in links (40) during exposure to a substantially powerful magnetic field of the MRI machine (90). Second, these variations may prevent or reduce demagnetization of magnets (120) during exposure to a substantially powerful magnetic field of the MRI machine (90). Third, these variations may prevent or reduce additional compressive forces against the LES (6) during exposure to a substantially powerful magnetic field of the MRI machine. After removal from the substantially powerful magnetic field of the MRI machine (90), the sphincter augmentation device incorporating beads (100) may continue operating as effectively as it did before being placed in the substantially powerful magnetic field of the MRI machine (90), without suffering any damage from being exposed to the substantially powerful magnetic field of the MRI machine (90).

III. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

EXAMPLE 1

An apparatus, the apparatus comprising: (a) a plurality of beads, wherein each bead comprises: (i) a housing, (ii) a passageway extending through the housing, wherein the passageway defines an axis, and (iii) at least one annular magnet, wherein the at least one annular magnet is coaxially positioned about the passageway, wherein the housing defines a gap adjacent to the at least one annular magnet, wherein the gap is sized and configured to allow at least one annular magnet to rotate relative to the housing about a rotation axis, wherein the rotation axis is offset from the axis of the passageway; and (b) a plurality of links joining the beads together, wherein portions of the links are slidably disposed in corresponding passageways of the beads.

EXAMPLE 2

The apparatus of Example 1, wherein the housing is formed of a non-ferrous material.

EXAMPLE 3

The apparatus of any one or more of Examples 1 through 2, wherein the passageway has an inner diameter, wherein the housing further includes a first opening at a first end of the passageway and a second opening at a second end of the passageway, wherein the first and second openings each have respective diameters that are less than the inner diameter of the passageway.

EXAMPLE 4

The apparatus of any one or more of Examples 1 through 3, wherein the at least one annular magnet comprises a rare earth magnet.

EXAMPLE 5

The apparatus of any one or more of Examples 1 through 4, wherein the housing further includes at least one internal boss structure, wherein the gap is defined between the at least one internal boss structure and the at least one annular magnet.

EXAMPLE 6

The apparatus of any one or more of Examples 1 through 5, wherein the rotation axis is perpendicular to the axis of the passageway.

EXAMPLE 7

The apparatus of any one or more of Examples 1 through 6, wherein each link is formed of a superelastic material.

EXAMPLE 8

The apparatus of Example 7, wherein the superelastic material comprises nitinol.

EXAMPLE 9

The apparatus of any one or more of Examples 1 through 8, wherein each link comprises: (i) a wire, (ii) a first ball end, wherein the first ball end is slidably disposed in the passageway of a first bead of the plurality of beads, and (iii) a second ball end, wherein the second ball end is slidably disposed in the passageway of a second bead of the plurality of beads, wherein the second bead is adjacent to the first bead.

EXAMPLE 10

The apparatus of Example 9, wherein the wire includes a preformed bend between the first and second ball ends.

EXAMPLE 11

The apparatus of any one or more of Examples 1 through 10, wherein beads are joined via the links in a linear array.

EXAMPLE 12

The apparatus of Example 11, further comprising: (a) a first attachment feature associated a with a first end of the linear array; and (b) a second attachment feature associated with a second end of the linear array, wherein the first and second attachment features are configured to be coupled together to form an annular arrangement of the beads and links.

EXAMPLE 13

The apparatus of Example 12, wherein the magnets of the beads are configured to impart a radially inwardly oriented magnetic bias to the annular arrangement.

EXAMPLE 14

The apparatus of Example 13, wherein the annular arrangement is sized and configured to fit around a lower esophageal sphincter.

EXAMPLE 15

The apparatus of Example 14, wherein the magnets of the beads are configured to magnetically bias an opening of the lower esophageal sphincter to a closed state, wherein the magnets of the beads are further configured to permit separation of the beads to thereby permit passage of a bolus through the opening of the lower esophageal sphincter.

EXAMPLE 16

An apparatus, the apparatus comprising: (a) a plurality of beads, wherein each bead comprises: (i) a housing defining an axis and a magnet receiving space, and (ii) at least one annular magnet, wherein the at least one annular magnet is coaxially positioned about the axis and in the magnet receiving space, wherein the magnet receiving space is sized to provide a gap adjacent to the at least one annular magnet, wherein the gap is sized and configured to allow at least one annular magnet to rotate relative to the housing about a rotation axis, wherein the rotation axis is offset from the axis of the housing; and (b) a plurality of links joining the beads together.

EXAMPLE 17

The apparatus of Example 16, wherein the beads are configured to slide relative to the links.

EXAMPLE 18

The apparatus of any one or more of Examples 16 through 17, wherein the housing is further configured to restrict rotation of the annular magnet relative to the housing about the rotation axis.

EXAMPLE 19

An apparatus, the apparatus comprising: (a) a plurality of beads, wherein each bead comprises: (i) a housing defining a longitudinal axis, and (ii) at least one annular magnet, wherein the at least one annular magnet is coaxially positioned in the housing about the longitudinal axis; (b) a plurality of links joining the beads together; and (c) a means for permitting the at least one annular magnet to rotate relative to the housing about a rotation axis, wherein the rotation axis is offset from the longitudinal axis of the housing.

EXAMPLE 20

The apparatus of Example 19, wherein an inserted portion of each link is positioned in a bead of the plurality of beads, wherein the inserted portion is positioned along the longitudinal axis of the housing of the corresponding bead.

EXAMPLE 21

An apparatus, the apparatus comprising: (a) a plurality of beads, wherein each bead comprises: (i) a housing, (ii) a passageway extending through the housing, wherein the passageway defines an axis, and (iii) at least one annular magnet, wherein the at least one annular magnet is coaxially positioned about the passageway; and (b) a plurality of links joining the beads together, wherein portions of the links are slidably disposed in corresponding passageways of the beads, wherein each link is formed of a superelastic material.

EXAMPLE 22

The apparatus of Example 21, wherein the housing defines a gap adjacent to the at least one annular magnet, wherein the gap is sized and configured to allow at least one annular magnet to rotate relative to the housing about a rotation axis, wherein the rotation axis is offset from the axis of the passageway.

IV. Miscellaneous

It should also be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus, the apparatus comprising:
    (a) a plurality of beads, wherein each said bead comprises:
        (i) a housing,
        (ii) a passageway extending through the housing, wherein the passageway defines an axis, and
        (iii) at least one annular magnet, wherein the at least one annular magnet is coaxially positioned about the passageway, wherein the at least one annular magnet includes a radially inner surface and a radially outer surface, one or both of the radially inner or outer surfaces being continually convex from a first lateral side of the at least one annular magnet to a second lateral side of the at least one annular magnet in a plane parallel to the axis,
        wherein the housing defines a gap adjacent to the at least one annular magnet, wherein the gap is sized and configured to allow the at least one annular magnet to rotate relative to the housing about a rotation axis, wherein the rotation axis is offset from the axis of the passageway; and
    (b) a plurality of links joining the beads together, wherein portions of the links are slidably disposed in corresponding passageways of the beads.

2. The apparatus of claim 1, wherein the housing is formed of a non-ferrous material.

3. The apparatus of claim 1, wherein the passageway has an inner diameter, wherein the housing further includes a first opening at a first end of the passageway and a second opening at a second end of the passageway, wherein the first and second openings each have respective diameters that are less than the inner diameter of the passageway.

4. The apparatus of claim 1, wherein the at least one annular magnet comprises a rare earth magnet.

5. The apparatus of claim 1, wherein the housing further includes at least one internal boss structure, wherein the gap is defined between the at least one internal boss structure and the at least one annular magnet.

6. The apparatus of claim 1, wherein the rotation axis is perpendicular to the axis of the passageway.

7. The apparatus of claim 1, wherein each said link is formed of a superelastic material.

8. The apparatus of claim 7, wherein the superelastic material comprises nitinol.

9. The apparatus of claim 1, wherein each said link comprises:
    (i) a wire,
    (ii) a first ball end, wherein the first ball end is slidably disposed in the passageway of a first bead of the plurality of beads, and
    (iii) a second ball end, wherein the second ball end is slidably disposed in the passageway of a second bead of the plurality of beads, wherein the second bead is adjacent to the first bead.

10. The apparatus of claim 9, wherein the wire includes a preformed bend between the first and second ball ends.

11. The apparatus of claim 1, wherein said beads are joined via the links in a linear array.

12. The apparatus of claim 11, further comprising:
    (a) a first attachment feature associated a with a first end of the linear array; and
    (b) a second attachment feature associated with a second end of the linear array, wherein the first and second attachment features are configured to be coupled together to form an annular arrangement of the beads and links.

13. The apparatus of claim 12, wherein the magnets of the beads are configured to impart a radially inwardly oriented magnetic bias to the annular arrangement.

14. The apparatus of claim 13, wherein the annular arrangement is sized and configured to fit around a lower esophageal sphincter.

15. The apparatus of claim 14, wherein the magnets of the beads are configured to magnetically bias an opening of the lower esophageal sphincter to a closed state, wherein the magnets of the beads are further configured to permit separation of the beads to thereby permit passage of a bolus through the opening of the lower esophageal sphincter.

16. An apparatus, the apparatus comprising:
(a) a plurality of beads, wherein each said bead comprises:
 (i) a housing defining an axis and a magnet receiving space, and
 (ii) at least one annular magnet, wherein the at least one annular magnet is coaxially positioned about the axis and in the magnet receiving space,
 wherein the magnet receiving space is sized to provide a gap adjacent to the at least one annular magnet, wherein the gap is sized and configured to allow the at least one annular magnet to rotate relative to the housing about a rotation axis, wherein the rotation axis is offset from the axis of the housing; and
(b) a plurality of links joining the beads together.

17. The apparatus of claim 16, wherein the beads are configured to slide relative to the links.

18. The apparatus of claim 16, wherein the housing is further configured to restrict rotation of the annular magnet relative to the housing about the rotation axis.

19. An apparatus, the apparatus comprising:
(a) a plurality of beads, wherein each said bead comprises:
 (i) a housing,
 (ii) a passageway extending through the housing, wherein the passageway defines an axis, and
 (iii) at least one annular magnet, wherein the at least one annular magnet is coaxially positioned about the passageway; and
(b) a plurality of links joining the beads together, wherein portions of the links are slidably disposed in corresponding passageways of the beads,
wherein the housing defines a gap adjacent to the at least one annular magnet, wherein the gap is sized and configured to allow the at least one annular magnet to rotate relative to the housing about a rotation axis, wherein the rotation axis is offset from the axis of the passageway.

20. The apparatus of claim 19, wherein each said link is formed of a superelastic material.

* * * * *